US010792344B2

(12) United States Patent
Marx et al.

(10) Patent No.: US 10,792,344 B2
(45) Date of Patent: *Oct. 6, 2020

(54) HIGH FREQUENCY APPLICATION OF BOTULINUM TOXIN THERAPY

(71) Applicant: MERZ PHARMA GmbH & CO. KGaA, Frankfurt am Main (DE)

(72) Inventors: Matthias Marx, Mannheim (DE); Susanne Grafe, Frankfurt am Main (DE); Reiner Benecke, Neu Thulendorf (DE); Dirk Dressler, Hamburg (DE)

(73) Assignee: MERZ PHARMA GmbH & CO. KGaA, Frankfurt am Main (DE)

( * ) Notice: Subject to any disclaimer, the term of this patent is extended or adjusted under 35 U.S.C. 154(b) by 334 days.

This patent is subject to a terminal disclaimer.

(21) Appl. No.: 15/403,670

(22) Filed: Jan. 11, 2017

(65) Prior Publication Data

US 2018/0193434 A1   Jul. 12, 2018
US 2019/0142912 A9   May 16, 2019

Related U.S. Application Data

(63) Continuation of application No. 14/749,834, filed on Jun. 25, 2015, now Pat. No. 9,572,871, which is a continuation of application No. 14/026,289, filed on Sep. 13, 2013, now Pat. No. 9,095,523, which is a continuation of application No. 11/824,393, filed on Jun. 29, 2007, now Pat. No. 8,557,255.

(60) Provisional application No. 60/817,756, filed on Jun. 29, 2006.

(51) Int. Cl.
| | |
|---|---|
| *A61K 38/48* | (2006.01) |
| *A61K 9/00* | (2006.01) |
| *A61K 47/32* | (2006.01) |
| *A61K 47/10* | (2017.01) |
| *A61K 47/36* | (2006.01) |

(52) U.S. Cl.
CPC ........ *A61K 38/4893* (2013.01); *A61K 9/0019* (2013.01); *C12Y 304/24069* (2013.01); *A61K 47/10* (2013.01); *A61K 47/32* (2013.01); *A61K 47/36* (2013.01); *Y02A 50/469* (2018.01)

(58) Field of Classification Search
None
See application file for complete search history.

(56) References Cited

U.S. PATENT DOCUMENTS

| | | | |
|---|---|---|---|
| 3,888,977 A | 6/1975 | Sanders | |
| 4,932,936 A | 6/1990 | Dykstra et al. | |
| 5,562,907 A | 10/1996 | Arnon | |
| 5,670,484 A | 9/1997 | Binder | |
| 6,306,423 B1 | 10/2001 | Donovan | |
| 6,383,509 B1 | 5/2002 | Donovan | |
| 6,573,241 B1 | 6/2003 | Bigalke | |
| 6,776,991 B2 | 8/2004 | Naumann | |
| 6,872,397 B2 | 3/2005 | Aoki | |
| 7,115,399 B2 | 10/2006 | Jenkins | |
| 7,211,261 B1 | 5/2007 | Moyer et al. | |
| 7,226,605 B2 | 6/2007 | Suskind et al. | |
| 7,288,259 B2 | 10/2007 | Sanders et al. | |
| 7,378,389 B2 | 5/2008 | Graham | |
| 7,964,199 B1 | 3/2011 | Bigalke | |
| 8,187,834 B2 | 5/2012 | Foster | |
| 8,343,508 B2 | 1/2013 | Pomato | |
| 8,557,255 B2 * | 10/2013 | Marx | A61K 38/4893 424/239.1 |
| 8,586,081 B2 | 11/2013 | Singh | |
| 9,095,523 B2 * | 8/2015 | Marx | A61K 38/4893 |
| 9,572,871 B2 * | 2/2017 | Marx | A61K 38/4893 |
| 2002/0010138 A1 | 1/2002 | Aoiki et al. | |
| 2002/0028216 A1 | 3/2002 | Donovan | |
| 2002/0028244 A1 | 3/2002 | Donovan | |
| 2002/0028765 A1 | 3/2002 | Maurer | |
| 2002/0168727 A1 | 11/2002 | Smith | |
| 2003/0180289 A1 | 9/2003 | Foster | |
| 2003/0219462 A1 | 11/2003 | Steward | |
| 2003/0224020 A1 | 12/2003 | Zabudkin | |
| 2004/0014663 A1 | 1/2004 | Aoki | |
| 2004/0028704 A1 | 2/2004 | Pappagallo | |
| 2004/0115222 A1 | 6/2004 | Kane | |
| 2004/0126380 A1 | 7/2004 | Schmidt | |
| 2004/0126397 A1 | 7/2004 | Aoki et al. | |
| 2004/0213812 A1 | 10/2004 | Ackerman | |
| 2005/0074466 A1 | 4/2005 | Suskind | |
| 2005/0106183 A1 | 5/2005 | Lamb | |

(Continued)

FOREIGN PATENT DOCUMENTS

| | | |
|---|---|---|
| CA | 2376193 | 12/2000 |
| CN | 1354670 | 12/2000 |

(Continued)

OTHER PUBLICATIONS

Poewe et al, J. Neurol. Neurosurg. Psychiatry, 1998. 64:13-17. (Year: 1998).*
Hyman et al, J. Neurol. Neurosurg. Psychiatry, 2000, 68:707-712 (Year: 2000).*
Cutus et al, Dermatologic Surgery. Nov. 2010, 36:1852-1858 (Year: 2010).*
"Arbeitskreis Botulinum toxin der DGN", website: www.botulinumtoxin.de/inddystonien.htm, p. 1, accessed Mar. 17, 2009.
"Summary of product characteristics, labelling, and package leaflet for Xeomin", xpil.medicines.org.uk/viewPil.aspx?DocID=20824.
Australian Application No. 2007264008, Office Action dated Feb. 16, 2012.

(Continued)

*Primary Examiner* — Nita M. Minnifield
(74) *Attorney, Agent, or Firm* — Hueschen and Sage

(57) ABSTRACT

The present invention relates to methods for treating diseases and disorders by administering a composition containing the neurotoxic component of a *Clostridium botulinum* toxin complex, wherein the composition is devoid of any other protein of the *Clostridium botulinum* toxin complex and wherein the composition is administered at short intervals and/or in high doses.

14 Claims, No Drawings

(56) References Cited

U.S. PATENT DOCUMENTS

| | | | |
|---|---|---|---|
| 2005/0142150 | A1 | 6/2005 | Graham |
| 2005/0159337 | A1 | 7/2005 | Schmidt |
| 2005/0208075 | A1 | 9/2005 | Borodic |
| 2005/0220820 | A1 | 10/2005 | Sanders |
| 2005/0232966 | A1 | 10/2005 | Hughes |
| 2005/0241652 | A1 | 11/2005 | Hanin |
| 2006/0057165 | A1 | 3/2006 | Dimitrakoudis |
| 2006/0067950 | A1 | 3/2006 | Taylor |
| 2006/0073208 | A1 | 4/2006 | First |
| 2006/0182767 | A1 | 8/2006 | Borodic |
| 2006/0269574 | A1 | 11/2006 | De Beer et al. |
| 2006/0286127 | A1 | 12/2006 | Van Schaack |
| 2007/0128226 | A1 | 6/2007 | Radovic |
| 2007/0160633 | A1 | 7/2007 | First et al. |
| 2007/0202129 | A1 | 8/2007 | Modi |
| 2007/0259391 | A1 | 11/2007 | Edelson |
| 2008/0081049 | A1 | 4/2008 | Sanders |
| 2008/0096822 | A1 | 4/2008 | Aoki |
| 2008/0220021 | A1 | 9/2008 | Modi |
| 2008/0279896 | A1 | 11/2008 | Heinen et al. |
| 2009/0028906 | A1 | 1/2009 | Grein |
| 2009/0162341 | A1 | 6/2009 | Foster |
| 2009/0186052 | A1 | 7/2009 | Cherif-Cheikh |
| 2009/0318360 | A1 | 12/2009 | Aoki |
| 2011/0217287 | A1 | 9/2011 | Bigalke |
| 2018/0147266 | A1* | 5/2018 | Pfeil .................. A61K 39/08 |
| 2019/0142912 | A9* | 5/2019 | Marx ................ A61K 38/4893 |
| 2019/0336691 | A1* | 11/2019 | Vogt ..................... A61M 5/24 |

FOREIGN PATENT DOCUMENTS

| | | |
|---|---|---|
| EP | 1366770 | 12/2003 |
| WO | WO0015245 | 3/2000 |
| WO | WO0074703 | 12/2000 |
| WO | WO 01/26736 | 4/2001 |
| WO | WO2004/016763 | 2/2004 |
| WO | WO 2004/098714 | 11/2004 |
| WO | WO 2005/035749 | 4/2005 |
| WO | WO2006059093 | 6/2006 |
| WO | WO2006094539 | 9/2006 |

OTHER PUBLICATIONS

Benecke, et al., A new Botulinum toxin type A free of complexing proteins for treatment of cervical dystonia, Neurology 2005, 64: 1949-1951.

Beneke Movement Disorders vol. 19, Suppl. 9, P291, 2004. Abstract.

Bulstrode, NW, et al., Aest. Plast. Surg. vol. 26, 356-359 (2002).

Canadian Application No. 2,654,214; Office Action dated Jul. 12, 2011.

Carruthers, et al. Plastic and Reconstructive Surgery, Nov. Supplement, pp. 1S-22S, 2004.

Carruthers, et al., Botulinum toxin type A, Journal of the American Academy of Dermatology, C.V. Mosby, St. Louis, MO, US, vol. 53, No. 2, Aug. 2, 2005; 284-290.

Catsicas, S., Grenningloh G., Pich, E.M.: Nerve terminal proteins; to fuse to learn. Transneuro Science 1994; 17: 368-379.

Childers, MK, et al., 1999, "Use of botulinum toxin type A in pain management: a clinician's guide".

Chile Search Report for Chile Patent Application No. 1911-2007, (2010).

China Office Action for China Patent Application No. 200780020682. 0, (2011).

Chinese office action for CN200780020682 dated Jul. 27, 2012.

Comella, Cynthia L. et al., Botulinum Toxins in Neurological Disease, Muscle & Nerve May 2004, 628-644.

Dasgupta BR, Sathyamoorthy V. Purification and amino acid composition of type A botulinum neurotoxin. Toxicon. 1984; 22(3):415-24.

Decision to refuse a European Patent application; EP Application 07764931.7, Mar. 2011.

Dressler D., Bigalke H. (2002) Botulinum toxin antibody titres after cessation of botulinum toxin therapy. Mov Disord 17:170-173.

Dressler, D., et al., (2005) The mouse diaphragm assay for detection of antibodies against botulinum toxin type B. Mov Diord 20: 1617-1619.

Dressler, D., et al., Xeomin (R): Perspective of a novel therapeutic botulinu toxin preparation, Aktuelle Neurologie, Thieme, Stuttgart, DE LNKD-DOI: 10. 1055/S-2005-915441, vol. 33. No. 3, Apr. 1, 2006, 138-141.

English Language Translation of Chinese Office Action for CN200780020682 dated Jul. 27, 2012.

English Language Translation of Israeli Office Action for IL195201 dated Aug. 26, 2012.

English Language Translation of Japan Office Action for JP2009-517002 dated Aug. 10, 2012.

Europe Office Action in European Patent Application No. EP 07 764 931.7, dated Mar. 24, 2011.

Europe Office Action in European Patent Application No. EP 07 764 931.7, dated Mar. 12, 2010.

Europe Office Action in European Patent Application No. EP 07 764 931.7, dated Oct. 15, 2010.

Fachinformation (SRZ) of Dec. 2009.

Fachinformation (SRZ) of Mar. 2006.

Fachinformation (SRZ) of Sep. 2008.

Fachinformation (SRZ), Jun. 2005.

Fahn S. Assessment of the Primary Dystonias. In: Munsat TL, editor. Quantification of Neurologic Deficit. Boston: Butterworths; 1989. p. 241-279.

Fahn, S., Assessment of the primary Dystonias. In: Munsat TL, editor. Quantification of Neurologic Deficit. Boston: Butterworths; 1989. p. 241-270.

Frankel et at. 1998, Arch. Otolaryngol Head Neck Surg. 124:321-323.

Goertelmeyer, R., et al., The Blepharospasm Disability Index (BSDI) for the Assessment of Functional Health in Focal Dystonia Clin. Neurophysiol. 2002; 113(1): S77-S78.

Göschel H, Wohlfarth K., Frevert J., Dengler R., Bigalke H. (1997) Exp Neurol. Sep. 1997; 147(1):96-102.

Grandas F, Elston J, Quinn N, Marsden CD. Blepharospasm: A review of 264 patients. J Neurol Neurosurg Psyciatry 1988; 51(6); 767-772.

Huang, W., et al., Pharmacology of botulinum toxin, Journal of the American Academy of Dermatology, C.V. Mosby, St. Louis, MO, US, vol. 43, No. 2, Part 1, Aug. 2000, pp. 249-259.

ISO10 A novel botulinum toxin A product (Merz Pharma GmbH & Co,. KGaA), Parkinsonism and Related Disorders, Elsevier Science, Oxford, GB, vol. 11, 2005, 266-266.

Israel Office Action in Israel Patent Application No. 195201, (dated 2010).

Israeli Office Action for IL95201 dated Aug. 26, 2012.

Jankovic J, Orman J. Blepharospasm: Demographic and clinical survey of 250 patients. Ann Ophthalmol 1984; 16(4): 371-376.

Japanese Application No. 2009-517002, Office Action, dated 2011.

Johnson, E.A., Biomedical aspectf of Botulinum Toxin, Journal of Toxicology. Toxin Reviews, Dekker, New York, NY, US, vol. 18, No. 1, Jan. 1, 1999; pp. 1-15.

Jost, WH et al., "Efficacy and tolerability of a botulinum toxin type A free of complexing proteins (NT 201) compared with commercially available botulinum toxin type A (BOTOX) in healthy volunteers" Journal of Neural transmission; vol. 112, No. 7, Jun. 1, 2005, 905-913.

Jost WH, Other indicationso f botulinum toxin therapy: European Journal of Neurology 2006 United Kingdom, vol. 13, No. Suppl. 1, Feb. 2006, 65-69.

Kessler KR, Skutta M., Benecke R., Long-term treatment of cervical dystonia with botulinum toxin A:efficacy, safety, and antibody frequency. German Dystonia Study Group. J Neurol. Apr. 1999; 246(4):265-74.

Kessler, KR., Skutta, M., Benecke, R., Long term treatment of cervical dystonia with botulinum toxin A: efficacy, safety, and antibody frequency. German Dystonia Study Group. J Neurol. Apr. 1999; 246(4):265-75.

(56) References Cited

OTHER PUBLICATIONS

Koman LA, Mooney JF, Smith BP, Goodman A, Mulvaney T. Management of spasticity in cerebral palsy with botulinum—A toxin: report of a preliminary, randomized, double-blind trial. J Pediatr Orthop 1994; 14(3): 299-303.
Maria G, Brisinda G. Civello IM, Bentivoglio AR, Sganga G, Albanese A. Relief by botulinum toxin of voiding dysfunction due to bening prostatic hyperplasia: results of a randomized, placebo-controlled study. Urology 2003; 62(2): 259-265.
Mauriello JA, Leone T, Dhillon S, Pakeman B, Mostafavi R, Yepez MC. Treatment choices of 119 patients with hemifacial spasm over 11 years. Clin Neurol Neurosurg 1996; 98(3): 213-216.
Merz, "Fachinformation (SRZ) XEOMIN", pp. 1-4; Jun. 2005.
Montecucco C., Shiavo G., Rosetto O: The mechanism of action of tetanus and botulinum neurotoxins. Arch Toxicol. 1996; 18 (Suppl.): 342-354.
Mueller J., Wissel J., Kemmler G., Bodner T., Poewe W., Quality of life in patients with craniocervical dystonia: development of the CCDQ-24, Mov. Disord. 2000; 15(Suppl 3): 761.
Neumann, M, et al., "Depletion of neutralising antibodies resensitises a secondary non-responder to botulinum a neurotoxin" Journal of Neurology Neurosurgery & Psychiatry, vol. 65, No. 6, Dec. 1998, 924-927.
Olney R.K., Aminoff M.J., Gelb D.J., Löwenstein D.H.: Myomuscular effects distant from the site of botulinum neurotoxin injection. Neurology 1988; 38: 1780-1783.
Pakistan Office Action for Pakistan Patent Application No. 776/207, (dated 2009).
Pakistan Office Action in Pakistan Patent Application No. 776/2007, (dated 2008).
Panama Office Action in Panama Patent Application No. 87344, (dated 2008).
Pearce L.B., Borodic GE, First ER, MacCallum RD (1994) Measurement of botulinum toxin activity: evaluation of the lethality assay. Toxicol Appl Pharmacol 128: 69-77.
Pidcock PS. The emerging role of therapeutic botulinum toxin in the treatment of cerebral palsy, J Pediatr 2004; 145(2 Suppl): S33-S35.
Roggenkamper Movement Disorders vol. 19, Suppl. 9, P208, 2004. Abstract.
Sakaguchi G. (1983) Clostridium botulinum toxins. Pharmacol Ther 19: 165-194.
Schantz & Kauter, 1978. Microbiological methods. Standardized assay for Clostridium botulinum neurotoxins. J Assoc Off Anal Chem 1978; 61(1):96-99.
Schurch B. De Seze M, Denys P, Chartier-Kastler E, Haab F, Everaert K, et al. Botulinum toxin type a is a safe and effective treatment for neurogenic urinary incontinence: results of a single treatment, randomized, placebo controlled 6-month study. J Urol 2005; 174(1): 196-200.
Schurch B. The role of botulinum toxin in neurourology. Drugs Today 2004; 40(3):205-212.
Simpson L.L., Ann Rev Pharrnacol Toxicol. 2004; 44:167-93.
Sugiyama H 1980 (Microbiological Reviews, p. 419-448).
Taiwanese Appliation No. 096123534, Office Action, English language translation, dated Dec. 20, 2012.
Taiwanese Application No. 096123534, Search Report, dated Dec. 20, 2012.
Taiwanese Application No. 096123534, Search Report, English language translation, dated Dec. 20, 2012.
Taiwanese Application No. 096123534, Office Action, dated Dec. 20, 2012.
Watkins CL, Leathley MJ, Gregson JM, Moore AR Smith TL, Sharma AK Prevalence of spasticity post stroke. Clin Rehabil 2002; 16(5): 515-522.
Welmer A.,., von Arbin M., Widen Holmqvist L., Sommerfeld D.K, Spasticity and its association with functioning and helath-related quality of life 18 months after stroke, Cerebrovasc. Dis, 2005; 21(4): 247-253.
"Arbeitskreis Botulinum toxin der DGN", website: www.botulinumtoxin.de/inddystonien.htm, p. 1, accessed Mar. 17, 2009: English language translation of penultimate paragraph of p. 1.
Merz, "Fachinformation (SRZ) Xeomin", pp. 1-4, Jun. 2005. English language translation of pp. 1-4.
Pierson. Susan H et al., Arch Phys Med Rehabil, vol. 77, Jul. 1996, Botulinum toxin A in the treatment of spasticity: Functional implications and patient selection.
Roggenkamper, P et al., Journal of neural Transmission, 2006, vol. 113, pp. 303-312, Efficacy and safety of a new Botulinum type A free of cornplexing proteins in the treatment of blepharospasm.

* cited by examiner

HIGH FREQUENCY APPLICATION OF BOTULINUM TOXIN THERAPY

FIELD OF INVENTION

The present invention relates to methods for treating diseases and disorders by administering a composition containing the neurotoxic component of a *Clostridium botulinum* toxin complex, wherein the composition is devoid of any other protein of the *Clostridium botulinum* toxin complex and wherein the composition is administered at short intervals and/or in high doses.

More particular, the present invention relates to a method of treating a disease or condition caused by or associated with hyperactive cholinergic innervation of muscles or exocrine glands in a patient, the method comprising administering a composition comprising an effective amount of a neurotoxic component of a *Clostridium botulinum* toxin complex, the composition being devoid of any other protein component of the *Clostridium botulinum* toxin complex, wherein (a) the patient is a human, (b) the composition is administered by injection, and (c) the composition is administered at an interval of less than three months, the interval comprising a first treatment and a second treatment, wherein the amount administered in the second treatment can be lower, higher or identical to the amount administered in the first treatment. The present invention also relates to a method of treating a disease or condition caused by or associated with a pathological activity of a muscle in a patient, the method comprising administering a composition comprising an effective amount of a neurotoxic component of a *Clostridium botulinum* toxin complex, the composition being devoid of any other protein component of the *Clostridium botulinum* toxin complex, wherein (a) the patient is a human with a severe movement disorder or severe spasticity; (b) the composition is administered by injection; and (c) the effective amount administered exceeds 500 U of neurotoxic component in adults or exceeds 15 U/kg body weight in children. Finally, the present invention also relates to a method of reducing facial lines or wrinkles of the skin or of removing facial asymmetries, the method comprising administering to an individual a composition comprising an effective amount of a neurotoxic component of a *Clostridium botulinum* toxin complex, the composition being devoid of any other protein component of the *Clostridium botulinum* toxin complex, wherein (a) the individual is a human; (b) the composition is administered by subcutaneous or intramuscular injection into, or in vicinity of, one or more facial muscles or muscles involved in the formation of the wrinkle of the skin or the asymmetry; and (c) the composition is administered at an interval of less than three months, the interval comprising a first treatment and a second treatment, wherein the amount administered in the second treatment can be lower, higher or identical to the amount administered in the first treatment.

BACKGROUND OF INVENTION

*Botulinum* toxin is produced by the bacterium *Clostridium*. There are seven antigenically distinct serotypes of *botulinum* toxin, namely *botulinum* toxin A, B, C, D, E, F and G. *Botulinum* toxins, when released from lysed *Clostridium* cultures are generally associated with other bacterial proteins, which together form of a toxin complex. The neurotoxic subunit of this complex is referred herein as the "neurotoxic component" of the *botulinum* toxin complex. The terms "*botulinum* toxin" or "*botulinum* toxins", refers to the neurotoxic component devoid of any other proteins clostridial proteins, but also to the "*botulinum* toxin complex": it is used herein in cases when no discrimination between the two states of the neurotoxic component is necessary or desired. This complex usually contains additional, so-called "non-toxic" proteins, which we will refer to as "complexing proteins" or "bacterial proteins". The complex of neurotoxic component and bacterial proteins is referred to as "*Clostridium botulinum* toxin complex" or "*botulinum* toxin complex". The molecular weight of this complex may vary from about 300,000 to about 900,000 Da. The complexing proteins are, for example, various hemagglutinins. The proteins of this toxin complex are not toxic themselves but provide stability to the neurotoxic component and are responsible for oral toxicity in *botulinum* intoxications. Unlike the toxin complex, the neurotoxic component in its isolated and pure form, i.e. devoid of any complexing *Clostridium* proteins, is acid labile and does not resist the aggressive environment in the gastrointestinal tract.

The neurotoxic component of the *botulinum* toxin complex is initially formed as a single polypeptide chain, having in the case of serotype A a molecular weight of approximately 150 kDa. In other serotypes the neurotoxic component has been observed to vary between about 145 and about 170 kDa, depending on the bacterial source. In the case of serotype A, for example, proteolytic processing of the polypeptide results in an activated polypeptide in the form of a dichain polypeptide, consisting of a heavy chain and a light chain, which are linked by a disulfide bond. In humans, the heavy chain mediates binding to pre-synaptic cholinergic nerve terminals and internalization of the toxin into the cell. The light chain is believed to be responsible for the toxic effects, acting as zink-endopeptidase and cleaving specific proteins responsible for membrane fusion (SNARE complex) (see e.g. Montecucco C., Shiavo G., Rosetto O: The mechanism of action of tetanus and *botulinum* neurotoxins. *Arch Toxicol.* 1996; 18 (Suppl.): 342-354)). By disrupting the process of membrane fusion within the cells, *Botulinum* toxins prevent the release of acetylcholine into the synaptic cleft. The overall effect of *Botulinum* toxin at the neuromuscular junction is to interrupt neuro-muscular transmission, and, in effect, de-nervate muscles. *Botulinum* toxin also has activity at other peripheral cholinergic synapses, causing a reduction of salivation or sweating.

Each serotype of *Botulinum* toxin binds to the serotype specific receptor sites on the pre-synaptic nerve terminal. The specificity of *Botulinum* toxin for cholinergic neurons is based on the high affinity of the heavy chain for the receptor sites on these nerve terminals (Ref.: Katsekas S., Gremminloh G., Pich E. M.: Nerve terminal proteins; to fuse to learn. *Transneuro Science* 1994; 17: 368-379).

Despite its toxic effects, *botulinum* toxin complex has been used as a therapeutic agent in a large number of diseases. *Botulinum* toxin serotype A was approved for human use in the United States in 1989 for the treatment of strabism, blepharospasm, and other disorders. It is commercially available as *Botulinum* toxin A protein complex, for example, under the tradename BOTOX (Allergan Inc) or under the tradename DYSPORT (Ipsen Ltd). For therapeutic application the complex is injected directly into the muscle to be treated. At physiological pH, the toxin is released from the protein complex and the desired pharmacological effect takes place. The effect of *Botulinum* toxin is only temporary, which is the reason why repeated administration of *Botulinum* toxin may be required to maintain a therapeutic affect. In a number of cases resistance to *Botulinum* toxin has been observed after repeated administration of the *Botulinum* toxin protein complex. Patients developed relevant levels of neutralizing antibodies directed against the neurotoxic component and blocking its activity (Göschel H, Wohlfarth K, Frevert J, Dengler R, Bigalke H. (1997) Exp Neurol. 1997 September; 147(1):96-102.). As a result, therapy with *botulinum* toxin complex is no longer effective in those patients (using e.g. Botox or Dysport). Subsequent applications of *Botulinum* toxin medicaments such as Botox or Dysport, is ineffective. The antibody titer may decrease if the treatment with *Botulinum* toxin protein complexes is suspended. However, the duration for which the treatment has to be suspended may be lengthy (see, for example, Dressler D, Bigalke H (2002) *Botulinum* toxin antibody titres after cessation of *botulinum* toxin therapy. Mov Disord 17:170-173).

Initially, resistance to the *Botulinum* toxin complex was considered uncommon. Subsequent reports suggested a frequency of approximately 5% of antibody-induced therapy failure of *botulinum* toxin therapy in patients treated for cervical dystonia (Ref.: Kessler K R, Skutta M, Benecke R., Long-term treatment of cervical dystonia with *botulinum* toxin A: efficacy, safety, and antibody frequency. German Dystonia Study Group. J Neurol. 1999 April; 246(4):265-74.). This observation was based on retrospective assessments of patients at a single location. Recently, however, a much more frequent incidence has been reported, suggesting that approximately 20% of the subjects treated are affected (Ref.: *The Muscular Nerve* May 2004, p. 630). Generally, it is believed that the risk for antibody induced therapy failure is strongly correlated with the administered single dose of *botulinum* toxin.

It is believed that proteins contained in the complex may reinforce the immune response. Another risk factor for antibody-induced complete failure of *botulinum* toxin therapy is the interinjection interval, i.e. the interval between subsequent injection series. It is therefore common practise to administer *Botulinum* toxin only once every three months to reduce the risk of antibody formation. Patients in which the effect of the *Botulinum* administration ceases to exist earlier may be treated by oral medications. Effectiveness of those oral medications, however, is limited.

Another disadvantageous effect of *Botulinum* toxin protein complexes is its regional or systemic spread following injections into the target muscles. Single-fibre electromyography (SF-EMG) has shown increased jitter in muscles distant from the injection site. For example, Alnty et al., 1988 (Alny R. K., Aminoff M. J., Gelb D. J., Löwenstein D. H.: Myomuscular effects distant from the site of *botulinum* neurotoxin injection. *Neurology* 1988; 38: 1780-1783) show that patients treated by injecting into the neck muscles have increased jitter and fiber density in muscles distant from the injection site. These abnormalities return to normal after approximately three to six months. Other evidence of systemic spread of *Botulinum* toxin following local injection is the occurrence of changes in cardiovascular reflexes and blood pressure. (Ref.: Alny R. K., Aminoff M. J., Gelb D. J., Löwenstein D. H.: Myomuscular effects distant from the site of *botulinum* neurotoxin injection. *Neurology* 1988; 38: 1780-1783).

In some patients, the administration of *botulinum* toxin protein complex at high doses may affect muscles not intended for treatment. For example, when treating blepharospasm with a *botulinum* toxin protein complex, spreading may affect the eye lid opening muscle causing ptosis.

Therefore, not only the risk of antibody formation but also the risk of systemic spread makes it necessary to administer *botulinum* toxin at comparatively low and thus potentially less effective doses. Consequently, physicians are strongly advised to administer BOTOX or DYSPORT not more often than once every three months. This applies in particular to patients that require high doses of *Botulinum* toxin.

In view of the above, it is an objective of the invention to provide a treatment for patients affected by the disorders mentioned herein, that allows administration of a therapeutic *botulinum* toxin preparation at reduced intervals and/or by using comparatively high doses. Since therapeutic *botulinum* toxin preparations are to be applied in specific target tissues (e.g. specific muscles or glands), it is an important requirement that its spread into neighboring tissue is limited. A final but not less important requirement is a reduced antigenicity of the therapeutic *botulinum* toxin preparation. It is also an objective of the invention to provide methods for treating a disease associated with a spastic or dystonic muscle with a suitable medicament at flexible and/or frequent intervals. Another objective of the invention is to provide a cosmetic treatment using the drug at frequent intervals with a reduced risk of antibody formation and/or reduced systemic spread.

Accordingly, the present invention relates to a method of treating a disease or condition caused by or associated with hyperactive cholinergic innervation of muscles or exocrine glands in a patient, the method comprising administering a composition comprising an effective amount of a neurotoxic component of a *Clostridium botulinum* toxin complex, the composition being devoid of any other protein component of the *Clostridium botulinum* toxin complex, wherein (a) the patient is a human, (b) the composition is administered by injection, and (c) the composition is administered at an interval of less than three months, the interval comprising a first treatment and a second treatment, wherein the amount administered in the second treatment can be lower, higher or identical to the amount administered in the first treatment.

It is noteworthy that the concept of the present invention, which involves the administration of the neurotoxic component of the *botulinum* toxin complex, generally allows the treatment of any condition which is associated with hyperactive cholinergic innervation of a muscle or an exocrine gland, where the neurotoxic component blocks acetylcholine secretion into the synaptic cleft. Therefore, treatment offered by the present invention may be directed at any of the following indications, most of which are described in detail in Dressler D (2000) (*Botulinum* Toxin Therapy. Thieme Verlag, Stuttgart, N.Y.):

dystonia
cranial dystonia
   blepharospasm
   oromandibular dystonia
      jaw opening type
      jaw closing type
   bruxism
   Meige syndrome
   lingual dystonia
   apraxia of eyelid opening
cervical dystonia
   antecollis
   retrocollis
   laterocollis
   torticollis
pharyngeal dystonia
laryngeal dystonia
   spasmodic dysphonia/adductor type
   spasmodic dysphonia/abductor type
   spasmodic dyspnea limb dystonia
  arm dystonia
    task specific dystonia
      writer's cramp
        musician's cramps
        golfer's cramp
  leg dystonia
    thigh adduction, thigh abduction
    knee flexion, knee extension
    ankle flexion, ankle extension
    equinovarus deformity
  foot dystonia
    striatal toe
    toe flexion
    toe extension
  axial dystonia
    pisa syndrome
    belly dancer dystonia
  segmental dystonia
  hemidystonia
  generalised dystonia
dystonia in lubag
dystonia in corticobasal degeneration
dystonia in lubag
tardive dystonia
dystonia in spinocerebellar ataxia
dystonia in Parkinson's disease
dystonia in Huntington's disease
dystonia in Hallervorden Spatz disease
dopa-induced dyskinesias/dopa-induced dystonia
tardive dyskinesias/tardive dystonia
paroxysmal dyskinesias/dystonias
  kinesiogenic
  non-kinesiogenic
  action-induced
palatal myoclonus
myoclonus
myokymia
rigidity
benign muscle cramps
hereditary chin trembling
paradoxic jaw muscle activity
hemimasticatory spasms
hypertrophic branchial myopathy
maseteric hypertrophy
tibialis anterior hypertrophy
nystagmus
oscillopsia
supranuclear gaze palsy
epilepsia partialis continua
planning of spasmodic torticollis operation
abductor vocal cord paralysis
recalcitant mutational dysphonia
upper oesophageal sphincter dysfunction
vocal fold granuloma
stuttering
Gilles de la Tourette syndrom
middle ear myoclonus
protective larynx closure
postlaryngectomy speech failure
protective ptosis
entropion
sphincter Odii dysfunction
pseudoachalasia
nonachalsia oesophageal motor disorders
vaginismus
postoperative immobilisation
tremor
bladder dysfunction
detrusor sphincter dyssynergia
bladder sphincter spasm
hemifacial spasm
reinnervation dyskinesias
cosmetic use
craw's feet
frowning
facial asymmetries
mentalis dimples
stiff person syndrome
tetanus
prostate hyperplasia
adipositas treatment
infantile cerebral palsy
strabismus
  mixed
  paralytic
  concomitant
  after retinal detachment surgery
  after cataract surgery
  in aphakia
  myositic strabismus
  myopathic strabismus
  dissociated vertical deviation
  as an adjunct to strabismus surgery
  esotropia
  exotropia
achalasia
anal fissures
exocrine gland hyperactivity
Frey syndrome
Crocodile Tears syndrome
hyperhidrosis
  axillar
  palmar
  plantar
rhinorrhea
relative hypersalivation
  in stroke
  in parkinsosn's
  in amyotrophic lateral sclerosis
spastic conditions
  in encephalitis and myelitis
    autoimmune processes
      multiple sclerosis
      transverse myelitis
      Devic syndrome
    viral infections
    bacterial infections
    parasitic infections
    fungal infections
  in hereditary spastic paraparesis
  postapoplectic syndrome
    hemispheric infarction
    brainstem infarction
    myelon infarction
  in central nervous system trauma
    hemispheric lesions
    brainstem lesions
    myelon lesion
  in central nervous system hemorrhage
    intracerebral hemorrhage
    subarachnoidal hemorrhage
    subdural hemorrhage
    intraspinal hemorrhage in neoplasias
  hemispheric tumors
  brainstem tumors
  myelon tumors Botulinum toxin is obtainable, for example, by cultivation of *Clostridium* bacteria. The preferred *Clostridium* species of the present invention is *Clostridium botulinum*. However, it is important to note that the neurotoxic component may be derived from any other bacterial species. Provided it is a functional homolog of the neurotoxic component derived from *Clostridium botulinum*. The composition used in the methods of the present invention will always contain the neurotoxic component devoid of any other *Clostridium botulinum* proteins. However, when producing the neurotoxic component, the toxin may be isolated from the bacteria as a complex containing the neurotoxic component, i.e. the protein responsible for the toxic effect in humans and other bacterial proteins. Subsequently, the neurotoxic component may be purified from the toxin complex. As used herein, the terms "toxin complex" or "*botulinum* toxin complex" or "*botulinum* neurotoxin complex" are interchangeable and refer to a high molecular weight complex comprising the neurotoxic component of approximately 150 kDa and, in addition, non-toxic proteins of *Clostridium botulinum*, including hemagglutinin and non-hemagglutinin proteins (Sakaguchi 1983; Sugiyama 1980).

The present invention envisages treating patients characterized by having a disease associated with hyperactive cholinergic innervation of muscles or exocrine glands. The term "patient" as used herein refers to patients who have never been exposed to *botulinum* toxin but also to patients who have been exposed to *botulinum* toxin. The latter patient may have developed antibodies directed against the *botulinum* toxin complex or its components. Such antibodies may be neutralizing antibodies. Preferably, the patients do not have an antibody titer above 7 mU, in particular a titer of neutralizing antibodies above 7 mU. The term "antibody titer not above . . . " means less than 7 mU, e.g. 1 mU to 6 mU or 0.01 mU to 1 mU.

The term "hyperactive cholinergic innervation", as used herein, relates to a synapse, which is characterized by an unusually high amount of acetylcholine release into the synaptic cleft. "Unusually high" relates to an increase of up to 25%, up to 50% or more with respect to a reference activity which may be obtained, for example, by comparing the release with the release at a synapse of the same type but which is not in a hyperactive state, wherein muscle dystonia may be indicative of the hyperactive state. "Up to 25%" means, for example, about 1% to about 25%. Methods for performing the required measurements are known in the art.

The term "about" as used in the context of the present invention means "approximately" or "nearly". In the context of numerical values, without committing to a strict numerical definition, the term may be construed to estimate a value that is +/−10% of the value or range indicated.

The terms "neurotoxic component" or "neurotoxin component" as used throughout the specification, relates to the subunit of the *botulinum* toxin complex which has a neurotoxic activity and which has a molecular weight of approximately 150 kDa in serotype A. The term "neurotoxic component" also includes the functional homologs found in the other serotypes of *Clostridium botulinum*. In a preferred embodiment of the present invention, the neurotoxic component is devoid of any other *C. botulinum* protein, preferably also of RNA potentially associated with the neurotoxic component. The neurotoxic component may be the single chain precursor protein of approximately 150 kDa or the proteolytically processed neurotoxic component, comprising the light chain ($L_c$) of approximately 50 kDa and the heavy chain ($H_c$) of approximately 100 kDa, which may be linked by one or more disulfide bonds (for a review see e.g. Simpson L L, Ann Rev Pharmacol Toxicol. 2004; 44:167-93). Those of skill in the art will appreciate that full biological activity is attained only after proteolytic activation, even though it is conceivable that the unprocessed precursor can exert some biological functions or be partially active. "Biological activity" refers to (a) receptor binding, (b) internalization, (c) translocation across the endosomal membrane into the cytosol, and/or (d) endoproteolytic cleavage of proteins involved in synaptic vesicle membrane fusion. In vitro assays for assessing biological activity include the mouse $LD_{50}$ assay and the mouse hemidiaphragm assay as described by Pearce L B, Borodic G E, First E R, MacCallum R D (1994) (Measurement of *botulinum* toxin activity: evaluation of the lethality assay. Toxicol Appl Pharmacol 128: 69-77) and Dressler D, Lange M, Bigalke H (2005) (The mouse diaphragm assay for detection of antibodies against *botulinum* toxin type B. Mov Disord 20:1617-1619).

The biological activity is commonly expressed in Mouse Units (MU). As used herein, 1 MU is the amount of neurotoxic component, which kills 50% of a specified mouse population after intraperitoneal injection, i.e. the mouse i.p. $LD_{50}$ (Schantz & Kauter, 1978). The terms "MU" and "Unit" or "U" are interchangeable. Alternatively, the biological activity may be expressed in Lethal Dose Units (LDU)/ng of protein (i.e. neurotoxic component). The term "MU" is used herein interchangeably with the terms "U" or "LDU".

The term "effective amount" means an amount of neurotoxic component, which, after administration, results in a partial or complete removal of disease symptoms. Effective amounts are generally in the range of 1 to 2000 MU but also doses of up to 5000 MU may be used. When high doses of neurotoxic component are to be administered to a patient, it may be beneficial to split the treatment into more than one treatment session. The term "more than one treatment session" means e.g. 2, 3, 4, 5, 6, 7, 8, 9 treatment sessions.

Preferably, the neurotoxic component used in the methods of the present invention is purified from a culture of *C. botulinum*. Methods for cultivating *C. botulinum* and purifying the toxin complex therefrom have been described in the art (Reviewed in Schantz & Kauter, 1978. Microbiological methods. Standardized assay for *Clostridium botulinum* neurotoxins. J Assoc Off Anal Chem 1978; 61(1):96-99.) The neurotoxic component may be purified from *C. botulinum* essentially as described in the method of DasGupta & Sathyamoorthy (DasGupta B R, Sathyamoorthy V. Purification and amino acid composition of type A *botulinum* neurotoxin. Toxicon. 1984; 22(3):415-24.). To this end, *Clostridium botulinum* type A is cultivated for example in a 20 l fermenter in a medium consisting of 2% proteose peptone, 1% yeast extract, 1% glucose and 0.05% sodium thioglycolate. After growth for 72 hours, the toxin is precipitated by adding 3 N sulfuric acid (final pH=3.5). The precipitated and centrifuged biomass is extracted with 0.2 M sodium phosphate buffer at pH 6.0. After removal of the nucleic acids by precipitation with protamine sulfate, the toxin is precipitated by adding ammonium sulfate. The precipitate which has been solubilized and dialyzed against 50 mM sodium phosphate at pH 6.0 is bound to a DEAE-Sephadex® column at the same pH and eluted with 150 mM NaCl. This is followed by a chromatography on a QAE-Sephadex® column which has been equilibrated with a 50 mM Tris/HCl buffer pH 7.9. The toxin is eluted via a NaCl gradient. In the last step, the toxin is chromatographed on SP-Sephadex® at pH 7.0. In this case, the bound toxin is eluted from the column using a NaCl gradient (0-300 mM). The purified toxin is analyzed by SDS-polyacrylamide gel electrophoresis (SDS-PAGE) and generally exhibits a purity of 95+/−5%.

Botulinum neurotoxins, in particular the toxin complex described above, have previously been classified into seven serologically distinct types A, B, C, D, E, F and G. In recent years, distinct populations of the A-(A1 and A2) and C-serotypes (C1 and C2) have been identified. Herein, these populations are designated as "subtypes".

The neurotoxic component of serotype A is commercially available under the trade name XEOMIN from Merz Pharmaceuticals in a composition that is devoid of any other proteins of the Clostridium botulinum toxin complex.

Alternatively, the neurotoxic component used in the methods of the present invention may be generated by recombinant gene expression. To this end, an open reading frame encoding the neurotoxic component or a mutant thereof may be cloned into a vector adapted for gene expression in a host cell of interest. Methods for recombinant gene expression and protein purification are known to the person skilled in the art.

The recombinant nucleic acid molecule encoding the neurotoxic component may be derived from a known nucleic acid sequence or may be recombined from two or more known sequences by recombinant techniques or chemical synthesis. An example of a chimeric neurotoxic component is a molecule generated by fusing e.g. the light chain of a first serotype to the heavy chain of a second serotype of the neurotoxic component. An example of chemical synthesis is the chemical synthesis of the entire neurotoxic component.

Also included are genetically modified neurotoxic components containing 1, 2, 3, 4, 5, 6, 7, 8, 9, 10 or up to 20 amino acid mutations. A mutation may be a substitution, an insertion or a deletion. Preferably, the mutation does not compromise any of the biological activities indicated above. However, it is also envisaged to use mutations to modulate the biological activity of the neurotoxic component.

Also included are the neurotoxic components of Botulinum toxins containing chemically modified amino acids, for example one or more amino acids which are glycosylated, acetylated or otherwise modified, which may be beneficial to the uptake or stability of the toxin. Particularly preferred is the lipidation of the neurotoxic component. Modifying residues may be added to the neurotoxic component e.g. by means of an enzymatic in vitro reaction or by using appropriate chemical reaction conditions. Alternatively, modifying enzymatic functions may be provided in trans by expressing the enzyme within the host cell.

Using the method described above allows significantly increasing the frequency of treatment without inducing neutralizing antibodies directed against the neurotoxic component. In this regard, it should be noted that prior to the present invention, known treatment regimens strictly avoided administration of botulinum toxin at intervals of less than three months, since a more frequent administration of botulinum toxin was thought to increase the likelihood of inducing an immune response in the patient treated. The examples disclosed herein support the notion that the use of the neurotoxic component instead of the botulinum toxin complex can avoid such problems.

In a preferred embodiment of the present invention, the second treatment is performed in order to improve the treatment effect of the first treatment. This will allow administration of appropriate botulinum toxin doses more efficiently. For example, in a first treatment session a suboptimal dose of the neurotoxic component may be administered. Should the patient's disease symptoms not sufficiently respond, more neurotoxic component may be administered in a second or in subsequent treatment session(s). Therefore, in view of the reduced risk associated with the methods of the present invention, a number of treatment sessions may be used in order to approach the optimal dose necessary to effectively treat a patient.

In accordance with the present invention, a first and a second and a subsequent treatment session may be scheduled at least one day after a preceding treatment session. The term "at least one day after" means e.g. 1, 2, 3, 4, 5, 6, 7, 8, 9 or 10 days or 1, 2, 3, 4, 5, 6, 7, 8, 9, 10, 11 or 12 weeks. However, it is also envisaged by the teaching of the present invention that the second treatment is scheduled only few hours after the first treatment, e.g. 2, 3, 4, 5, 6, 7 or 8 hours later.

In a preferred embodiment, the second (subsequent) treatment is carried out at a point in time when the efficacy of the first (previous) treatment begins to decline. With such a treatment regimen, a stable quality of life for the patients can be achieved.

The determination of the parameter "stable quality of life" for the patients is exemplarily described hereinunder by reference to one condition to be treated according to the present invention, namely blepharospasm, on the basis of the so-called Blepharospasm Disability Index (BSDI). The Blepharospasm Disability Index [BSDI] is a self-rating scale for assessment of impairment of specific activities of daily living caused by BEB Goertelmeyer R, Brinkmann S, Comes G, Delcker A, The Blepharospasm Disability Index (BSDI) for the Assessment of Functional Health in Focal Dystonia, Clin. Neurophysiol. 2002; 113(1): S77-S78.

The scale is to be answered by the patient at each visit. It includes 6 items to be assessed with a 5-point listing (i.e., 0-4 points per item) ranging from "no impairment, "slight/moderate/severe impairment" and "no longer possible due to my illness". The 6 items are "Driving a vehicle", "Reading", "Watching TV", "Shopping", "Walking" and "Doing everyday activities". Unlike other functional scales, which ignore scaling in case of non-applicable items, the BSDI allows for answering as 'not applicable' for five items except "Doing everyday activities"

The BSDI mean score for non-missing items is calculated by adding all applicable and answered items, and dividing by the number of items answered.

However, such parameters are available for many other diseases and conditions to be treated within the present invention, e. g. craniocervical dystonia questionnaire (CCDQ 24) for cervical dystonia (Mueller J, Wissel J, Kemmler G, Bodner T, Poewe W, Quality of life in patients with craniocervical dystonia: development of the CCDQ-24, Mov. Disord. 2000; 15(Suppl 3): 761, and HRQL, by the Swedish Short Form 36 Health Survey Questionnaire (SF-36) for spasticity (Welmer A K, von Arbin M, Widen Holmqvist L, Sommerfeld D K, Spasticity and its association with functioning and health-related quality of life 18 months after stroke, Cerebrovasc. Dis. 2006; 21(4): 247-253).

At each of the re-injection treatment or last treatment of the patient, the difference $\Delta_{BSDI}$ between the actual BSDI observation and the BSDI value at baseline will be calculated:

$$\Delta_{BSDI} = BSDI_{actual} - BSDI_{baseline}$$

The $BSDI_{baseline}$ is determined during the first visit of the patient to be treated and before the first injection of the medicament. The $BSDI_{actual}$ is determined after the respective (re)-injection of the medicament and 3 weeks thereafter, respectively.

On the basis of the $\Delta_{BSDI}$ value recorded at the first treatment, each patient will be allocated to one of three strata in the following way:

Stratum 1 (moderate improvement): $-1.00 \leq \Delta_{BSDI} \leq -0.65$
Stratum 2 (marked improvement): $-1.35 \leq \Delta_{BSDI} < -1.00$
Stratum 3 (abolishment of signs and symptoms): $\Delta_{BSDI} < -1.35$ A patient is classified as a responder, i.e., the patient demonstrates a stable level of quality of life, if none of the $\Delta_{BSDI}$ values calculated exceeds a threshold $\Delta_c$. The value of the threshold $\Delta_c$ depends on the stratum the patient belongs to. The values of the thresholds are:

Stratum 1: $\Delta_c = -0.40$
Stratum 2: $\Delta_c = -0.75$
Stratum 3: $\Delta_c = -1.10$ Responders show a reduction of their baseline BSDI value, and therefore an improvement of their quality of life status. The minimal magnitude of the improvement is given by the threshold $\Delta_c$. The values of $\Delta_c$ decrease with the number of the stratum because patients in Stratum 2 show a stronger response to the initial injection than patients in Stratum 1 (resulting in lower BSDI differences), and patients in Stratum 3 react even stronger than patients in Stratum 2.

Finally, the observed differences between the BSDI level at the day of a re-injection treatment and the baseline BSDI level will be analyzed to investigate if there is any improvement over time of the quality of life level at the time of re-injection (expected time of waning of treatment effect).

As used throughout the specification of the present invention, the term "total amount injected per treatment" refers to the total dosage and means the sum of neurotoxin applied to a patient during a single treatment. A single treatment may involve one or more injections. For example the treatment of *M. sternocleidomastoideus, M. splenius* capitis, *M. semispinalis* capitis and *M. trapezius* may involve 1, 2, 3, 4 or 5 injections, whereas the treatment of *M. levator* scapulae or *M. scaleni* may involve only 1 to 3 injections. As pointed out herein before, the amount used for treatment is dependent on a number of parameters, which are known in the art. Such parameters include for example the serotype of the neurotoxic component, the target tissue to be injected and a number of patient specific factors. It is envisaged by the teaching of the present invention that a single treatment may be split into two or more treatment sessions during which the above mentioned total amount of neurotoxic component is administered. This will be particularly the case if large amounts of neurotoxic component are to be administered.

Moreover, based on this embodiment of the present invention's method it will now be possible to more effectively treat a patient in need of an additional administration of the neurotoxic component. This may be the case, e.g. when, after a first or previous treatment, it is established that additional muscles contribute to the disease symptoms or when muscles have been missed.

In another preferred embodiment of the present invention, the patient is a patient requiring high doses of neurotoxic component. In another preferred embodiment of the present invention, (a) the patient is a patient with a severe movement disorder or severe spasticity and (b) the effective amount administered exceeds 500 U of neurotoxic component in adults or exceeds 15 U/Kg body weight in children.

Based on the embodiment of the present invention, it is now possible to treat patients with far greater amounts of neurotoxic component. In adult patients, such amounts may for example exceed 500 U of neurotoxic component.

As used throughout the present invention, an amount exceeding 500 U is for example an amount of more than 500 U and up to 550 U, up to 600 U, up to 700 U, up to 800 U, up to 900 U, up to 1000 U, up to 1100 U, up to 1200 U, up to 1300 U, up to 1400 U, up to 1500 U, up to 1600 U, up to 1700 U, up to 1800 U, up to 1900 U, or up to 2000 U. Preferably, the dose administered is in the range of 500 to 900 U, more preferably approximately 850 U. In children, "high amounts" means amounts exceeding 15 U/kg and up to 16 U/kg, up to 17 U/kg, up to 18 U/kg, up to 19 U/kg, up to 20 U/kg.

In a more preferred embodiment of the present invention, the amount which exceeds 500 U is a total amount in adults or 15 U/kg body weight in children and the amount is administered by (a) injecting a first fraction of this amount during a first treatment session and (b) injecting the remaining fraction during one or more subsequent treatment session(s), wherein the subsequent treatment session(s) is/are scheduled at least one day after the first treatment session. The total effective amount of neurotoxic component may be administered on the same day or on different days, i.e. in different treatment sessions. Preferably, when high amounts of neurotoxic component are to be administered, the total amount to be administered may be split and administered in two or more treatment sessions. This way, large amounts, which would otherwise not be compliant when administered in a single treatment session, may be administered to a patient without observing significant adverse effects.

In another preferred embodiment of the present invention, the patient is a human, who has been treated with *Botulinum* toxin but who complains about a decrease of the treatment effect and who requires treatment before expiry of 3 months after the treatment.

Such decreases of the therapeutic effect can be monitored by treatment calendars in which the patient records the severity of his disorder on a day-to-day basis (such treatment calendars are, for example, distributed by Merz Pharmaceuticals).

In yet another preferred embodiment of the present invention, the hyperactive gland is an autonomic exocrine gland and the composition is injected into or in the vicinity of that gland.

In a preferred embodiment, the autonomous exocrine gland is (a) selected from the group consisting of sweat gland, tear gland, salivary gland and mucosal gland; or (b) a hyperactive gland which is associated with a disease or condition selected from the group consisting of Frey syndrome, Crocodile Tears syndrome, axillar hyperhidrosis, palmar hyperhidrosis, plantar hyperhidrosis, hyperhidrosis of the head and neck, hyperhidrosis of the body, rhinorrhea, or relative hypersalivation in patients with stroke, Parkinson's disease or Amyotrophic Lateral Sclerosis. It is, however, to be noted that the target tissue of therapy of the neurotoxic component covers any exocrine gland with hyperactivity. Accordingly, it is envisaged that the present invention can be applied to the treatment involving any of the glands mentioned in Sobotta, Johannes: (Atlas der Anatomie des Menschen. 22. Auflage. Band 1 and 2. Urban & Fischer, 2005), which is incorporated herein by reference.

The present invention also relates to a method of treating a disease or condition caused by or associated with a pathological activity of a muscle in a patient, the method comprising administering a composition comprising an effective amount of a neurotoxic component of a *Clostridium botulinum* toxin complex, the composition being devoid of any other protein component of the *Clostridium botulinum* toxin complex, wherein (a) the patient is a human with a severe movement disorder or severe spasticity; (b) the composition is administered by injection; and (c) the effective amount administered exceeds 500 U of neurotoxic component in adults or exceeds 15 U/kg body weight in children.

In a preferred embodiment of the present invention, the amount which exceeds 500 U is a total amount in adults or 15 U/kg body weight in children and wherein the amount is administered by (a) injecting a first fraction of this amount during a first treatment session and (b) injecting the remaining fraction during one or more subsequent treatment session(s), wherein the subsequent treatment session is scheduled at least one day after the first treatment session.

In another preferred embodiment of the present invention, the composition is administered at an interval of less than three months, the interval comprising a first treatment and a second treatment, wherein the amount administered in the second treatment can be lower, higher or identical to the amount administered in the first treatment.

In yet another preferred embodiment of the present invention, the disease or condition is or involves dystonia of a muscle. The term "disease or condition which is or involves dystonia or dystonia of a muscle" refers to a condition involving a dystonic muscle. Preferably the condition is selected from the group consisting of generalized dystonia, segmental dystonia, focal dystonia, multifocal dystonia and hemidystonia. Focal dystonia is preferably selected from the group consisting of cranial dystonia, cervical dystonia, dystonia of the limbs, dystonia of the trunk, and spasmodic dysphonia. Cervical dystonia, also referred to as spasmodic torticollis, is characterized by involuntary, inappropriate muscle hyperactivity in muscles of the neck and the shoulder, leading to abnormal head movements and postures, jerks or tremor (Fahn S. Assessment of the Primary Dystonias. In: Munsat T L, editor. Quantification of Neurologic Deficit. Boston: Butterworths; 1989. p. 241-270. (ID 1760137)). Injection of the neurotoxic component in the affected neck and shoulder muscles leads to a significant relief of symptoms in most patients.

In a more preferred embodiment of the present invention, the dystonia is (a) selected from the group consisting of (1) cranial dystonia including blepharospasm, oromandibular dystonia of the jaw opening or jaw closing type, bruxism, Meige syndrome, lingual dystonia, apraxia of eyelid opening, (2) cervical dystonia including antecollis, retrocollis, laterocollis, torticollis (3) pharyngeal dystonia, (4) laryngeal dystonia including spasmodic dysphonia of the adductor type or of the abductor type, spasmodic dyspnea, (5) limb dystonia including arm dystonia such as task specific dystonias, including writer's cramp, musician's cramps or golfer's cramp, leg dystonia involving thigh adduction, thigh abduction, knee flexion, knee extension, ankle flexion, ankle extension or equinovarus deformity, foot dystonia involving striatal toe, toe flexion or toe extension, axial dystonia such as Pisa syndrome or belly dancer dystonia, segmental dystonia, hemidystonia or generalised dystonia, (6) dystonia in Lubag, (7) dystonia in corticobasal degeneration (8) tardive dystonia, (9) dystonia in spinocerebellar ataxia, (10) dystonia in Parkinson's disease, (11) dystonia in Huntington's disease, (12) dystonia in Hallervorden Spatz disease, (13) dopa-induced dyskinesias/dopa-induced dystonia, (14) tardive dyskinesias/tardive dystonia, (15) paroxysmal dyskinesias/dystonias (kinesiogenic, non-kinesiogenic, action-induced); or (b) involves a clinical pattern selected from the group consisting of torticollis, laterocollis, retrocollis, anterocollis, flexed elbow, pronated forearm, flexed wrist, thumb-in-palm or clenched fist.

The following table provides a non-limiting list of clinical patterns and the muscles potentially involved, the muscles being preferred target muscles in accordance with the teaching of the present invention.

| Clinical Pattern | Potential Target Muscles |
| --- | --- |
| Torticollis | splenius capitis, sternocleidomastoid, trapezius |
| Laterocollis | sternocleidomastoid, splenius capitis, scalene complex, levator scapulae |
| Retrocollis | splenius capitis, trapezius-pars cervicalis |
| Anterocollis | sternocleidomastoid, scalene complex, submental complex, suprahyoidal and infrahyoidal muscles |

"Spasmodic dysphonia" is a voice disorder caused by involuntary movements of one or more muscles of the larynx. Patients affected by spasmodic dysphonia have difficulty talking. Spasmodic dysphonia causes the voice to break or to have a tight, strained, strangled or effortful quality. As disclosed herein, injection of the neurotoxic component into the affected muscles of the larynx generally improves the voice.

Blepharospasm, is a progressive disease characterized by spontaneous, bilateral, intermittent or persistent involuntary contractions of the orbicular oculi muscles (Grandas F, Elston J, Quinn N, Marsden C D. Blepharospasm: A review of 264 patients. J Neurol Neurosurg Psychiatry 1988; 51(6): 767-772. (ID 1759120); Jankovic J, Orman J. Blepharospasm: Demographic and clinical survey of 250 patients. Ann Ophthalmol 1984; 16(4): 371-376. (ID 1761786); Mauriello J A, Leone T, Dhillon S, Pakeman B, Mostafavi R, Yepez M C. Treatment choices of 119 patients with hemifacial spasm over 11 years. Clin Neurol Neurosurg 1996; 98(3): 213-216. (ID 1777068)). Given as a local injection in the orbicularis oculi muscles, on the basis of the methods of the present invention, *Botulinum* toxin is a highly effective and well tolerated symptomatic treatment of blepharospasm.

In another preferred embodiment, patients with benign essential blepharospasm who are pre-treated with *botulinum* toxin type A who show a short duration of efficacy, are treated with *botulinum* neurotoxin free of complexing proteins by administration of said *botulinum* neurotoxin in shortened injection intervals, i.e. in intervals of less than three months. Preferably, the *botulinum* neurotoxin free of complexing proteins is highly purified *botulinum* neurotoxin type A. A new injection with *botulinum* neurotoxin is indicated when the patient reports a decline in treatment effect. Due to said treatment regimen, said patients can achieve a stable quality of life as discussed hereinbefore, which is preferably determined as discussed hereinbefore.

In a more preferred embodiment of the present invention, the muscle is selected from the group consisting of Ipsilateral splenius, contralateral sternocleidomastoid, ipsilateral sternocleidomastoid, splenius capitis, scalene complex, levator scapulae, postvertebralis, ipsilateral trapezius, levator scapulae, bilateral splenius capitis, upper trapezius, deep postvertebralis, bilateral sternocleidomastoid, scalene complex, submental complex, brachioradialis, bicepsbrachialis, pronator quadratus, pronator teres, flexor carpi radialis, flexor carpi ulnaris, flexor pollicis longus adductor pollicis, flexor pollicis brevis/opponens, flexor digitorum superficialisflexor digitorum profundus.

In a preferred embodiment of the present invention, the disease or condition is or involves spasticity of a muscle.

In a more preferred embodiment of the present invention, the spasticity is or is associated with (a) post-stroke spasticity, spasticity caused by cerebral palsy; or (b) (1) a spastic condition in encephalitis and myelitis relating to (a) autoimmune processes including respect to multiple sclerosis, transverse myelitis, Devic syndrome, (b) viral infections, (c) bacterial infections, (d) parasitic infections or (e) fungal infections, (2) hereditary spastic paraparesis, (3) postapoplectic syndrome resulting from hemispheric infarction, brainstem infarction or, myelon infarction, (4) a central nervous system trauma involving e.g. a hemispheric lesion, a brainstem lesion, a myelon lesion, (5) a central nervous system hemorrhage such as an intracerebral hemorrhage, a subarachnoidal hemorrhage, a subdural hemorrhage or an intraspinal hemorrhage, or (6) a neoplasia, e.g. a hemispheric tumor, a brainstem tumors or a myelon tumor. Other treatments may be the treatment of urinary bladder, spastic bladder, incontinence, spastic sphincter, spasticity caused by cerebral palsy or prostatic hyperplasia.

The term "post-stroke spasticity" relates to spasticity occurring after a stroke incident. Stroke is a leading cause of long-term disability, with spasticity occurring in 19% (2) to 38% of patients (Watkins C L, Leathley M J, Gregson J M, Moore A P, Smith T L, Sharma A K. Prevalence of spasticity post stroke. Clin Rehabil 2002; 16(5): 515-522. (ID 1915001)). Spasticity is defined as a motor disorder characterized by a velocity-dependent increase in tonic stretch reflexes (muscle tone) with exaggerated tendon jerks, resulting from hyperexcitability of the stretch reflex, as one component of the upper motor neuron syndrome (4). In some patients spasticity can be beneficial, as in the case of hip and knee extensor spasticity, which may allow weight bearing, with the affected limb acting like a splint (5). However, in the majority of patients spasticity causes difficulties with activities of daily living, such as dressing and cleaning the palm of the clenched hand (6). In accordance with the teaching of the present invention, common clinical patterns of deformity associated with spasticity in the corresponding muscle groups are treated with the neurotoxic component.

The term "urinary bladder" relates to a disorder of the bladder often, but not necessarily, resulting from a spinal cord lesion or multiple sclerosis or trauma resulting in incontinence and deteriorated voiding of urine. Preferably, the target muscle of neurotoxin administration is the striated sphincter urethrae muscle as described elsewhere (Schurch B. The role of *botulinum* toxin in neurourology. Drugs Today 2004; 40(3): 205-212. (ID 3097145); Schurch B, De Sèze M, Denys P, Chartier-Kastler E, Haab F, Everaert K, et al. *Botulinum* toxin type a is a safe and effective treatment for neurogenic urinary incontinence: results of a single treatment, randomized, placebo controlled 6-month study. J Urol 2005; 174(1): 196-200. (ID 3528462)).

The term "incontinence" means urinary incontinence, which is the inability to control the flow of urine from the bladder. There are various kinds and degrees of incontinence, which are within the scope of the teaching of the present invention: overflow incontinence is a condition in which the bladder retains urine after voiding; as a consequence, the bladder remains full most of the time, resulting in involuntary seepage of urine from the bladder; stress incontinence is the involuntary discharge of urine when there is increased pressure upon the bladder, as in coughing or straining to lift heavy objects; total incontinence is the inability to voluntarily exercise control over the sphincters of the bladder neck and urethra, resulting in total loss of retentive ability. In the treatment of incontinence, the composition mentioned herein may for example be injected cystoscopically into the detrusor muscle, excluding the trigonal region (Schurch B. The role of *botulinum* toxin in neurourology. Drugs Today 2004; 40(3): 205-212. (ID 3097145); Schurch B, De Sèze M, Denys P, Chartier-Kastler E, Haab F, Everaert K, et al. *Botulinum* toxin type a is a safe and effective treatment for neurogenic urinary incontinence: results of a single treatment, randomized, placebo controlled 6-month study. J Urol 2005; 174(1): 196-200. (ID 3528462)).

The term "prostatic hyperplasia" refers to an enlargement of the prostate in which the normal elements of the prostate gland grow in size and number. Their sheer bulk may compress the urethra, which courses through the center of the prostate, impeding the flow of urine from the bladder through the urethra to the outside. This may lead to urine retention and the need for frequent urination. If prostatic hyperplasia is severe, complete blockage may occur. After injecting the composition described herein into the prostate, a significant reduction of symptoms, serum markers of the prostate, prostate volume, post-void residual urine volume, and peak urinary flow rates are observed. Similar results have been described elsewhere (Maria G, Brisinda G, Civello I M, Bentivoglio A R, Sganga G, Albanese A. Relief by *botulinum* toxin of voiding dysfunction due to benign prostatic hyperplasia: results of a randomized, placebo-controlled study. Urology 2003; 62(2): 259-265. (ID 2562820)).

"Cerebral palsy" describes a wide spectrum of pyramidal dysfunctions causing paresis, extrapyramidal dysfunctions causing dystonia, rigidity, spasticity and spasms, apraxic components and coordinative dysfunctions. Cerebral palsy (Koman L A, Mooney J F, Smith B P, Goodman A, Mulvaney T. Management of spasticity in cerebral palsy with *botulinum*—A toxin: report of a preliminary, randomized, double-blind trial. J Pediatr Orthop 1994; 14(3): 299-303. (ID 1767458); Pidcock F S. The emerging role of therapeutic *botulinum* toxin in the treatment of cerebral palsy. J Pediatr 2004; 145(2 Suppl): S33-S35. (ID 2994781)) may occur after brain hemorrhage, asphyxia, premature birth and other perinatal complications. It is a life-long condition causing uncoordinated movements, paresis and various forms of muscle hyperactivity. Patients affected by cerebral palsy, when treated in accordance with the methods disclosed herein, experience a functional improvement of hyperactive muscles.

In a more preferred embodiment of the present invention, the spastic muscle is a smooth or striated muscle. Target tissue for the neurotoxic component in the treatment of muscle hyperactivity disorders can be in principle all striated and smooth muscles of the human body as described in Sobotta, Johannes: Atlas der Anatomie des Menschen. 22. Auflage. Band 1 and 2. Urban & Fischer, 2005. The muscles mentioned in this reference are incorporated herein by reference. The methods of the present invention may target any of these muscles.

The present invention also relates to a method of reducing facial lines or wrinkles of the skin or of removing facial asymmetries, the method comprising administering to an individual a composition comprising an effective amount of a neurotoxic component of a *Clostridium botulinum* toxin complex, the composition being devoid of any other protein component of the *Clostridium botulinum* toxin complex, wherein (a) the individual is a human; (b) the composition is administered by subcutaneous or intramuscular injection into, or in vicinity of, one or more facial muscles or muscles involved in the formation of the wrinkle of the skin or the asymmetry; and (c) the composition is administered at an interval of less than three months, the interval comprising a first treatment and a second treatment, wherein the amount administered in the second treatment can be lower, higher or identical to the amount administered in the first treatment.

This method of the present invention allows treating facial muscles or wrinkles of a patient's skin or a facial asymmetry. Typically, smaller amounts of neurotoxic component are used in such cosmetic treatment. Such amounts are preferably in the range of 1 to 5, 5 to 10, 10 to 20 or 20 to 50 Units. Such total amounts may be administered on the same day or on a subsequent day of treatment. For example, during a first treatment session a first fraction of the dose may be administered. This first fraction is preferably a suboptimal fraction, i.e. a fraction, which does not remove the wrinkles or skin lines completely. During one or more treatment sessions, the remaining fraction of the total dose may be administered.

In a preferred embodiment of the present invention, the composition is injected into the frown lines, horizontal forehead lines, crow's feet, perioral folds, mental ceases, popply chin, and/or platysmal bands.

In another preferred embodiment of the present invention, said muscle is selected from the group consisting of the following muscles: splenius capitis, sternocleidomastoid, scalene complex, levator scapulae, semispinalis, longissimus capitis, longissimus cervicis, multifidus, obliqus capitis inferior, obliqus capitis superior, rectus capitis posterior major, rectus capitis posterior minor, trapezius/pars horizontalis, trapezius/pars cervicalis, suprahyoidal muscles, infrahyoidal muscles, digastricus, pterygoideus medialis, pterygoideus lateralis, masseter, temporalis, orbicularis oculi, nasalis, procerus, corrugator supercilii, depressor anguli oris, depressor labii inferioris, frontalis, levator labii superioris, levator labii superioris alaeque nasi, orbicularis oris, risorius, zygomaticusminor, zygomaticus major, deltoideus, triceps brachii, brachioradialis, biceps brachii, pronator quadratus, pronator teres, flexor carpi radialis, flexor carpi ulnaris, flexor pollicis longus, opponens, interossei, lumbricales, adductor pollicis, flexor pollicis brevis, flexor digitorum superficialis, flexor digitorum profundus, adductor group, quadriceps femoris, hamstrings, triceps surae, tibialis posterior, flexor hallucis longus, tibialis anterior, extensor hallucis longus, extensor digitorum longus, flexor hallucis brevis, flexor digitorum brevis, paraverterbal muscles.

The neurotoxic component referred to herein above, may be part of a composition or pharmaceutical composition. This pharmaceutical composition may contain additional pharmaceutically active components. "Pharmaceutical composition" is a formulation in which an active ingredient for use as a medicament or diagnostic is contained or comprised. Such pharmaceutical composition may be suitable for diagnostic or therapeutic administration (i.e. by intramuscular or subcutaneous injection) to a human patient. The pharmaceutical composition may be lyophilized or vacuum dried, reconstituted, or in solution. When reconstituted it is preferred that the reconstituted solution is prepared adding sterile physiological saline (0.9% NaCl).

Such composition may comprise additional components such as a pH buffer, excipient, diluent, cryoprotectant and/or stabilizer.

"pH buffer" refers to a chemical substance being capable to adjust the pH value of a composition, solution and the like to a certain value or to a certain pH range.

"Stabilizing", stabilizes" or "stabilization" means that the active ingredient, i.e., the neurotoxic component in a reconstituted or aqueous solution pharmaceutical composition has greater than about 20%, 30%, 40%, 50%, 60%, 70%, 80%, 90%, and up to about 100% of the toxicity that the biologically active neurotoxic component had prior to being incorporated into the pharmaceutical composition. The activity of the preparation may be determined as described elsewhere herein.

"Cryoprotectant" refers to excipients which result in the active ingredient, i.e., a neurotoxic component in a reconstituted or aqueous solution pharmaceutical composition has greater than about 20%, 30%, 40%, 50%, 60%, 70%, 80%, 90%, and up to about 100% of the toxicity that the biologically active neurotoxic component had prior to being freeze-dried in the pharmaceutical composition. The activity of the preparation may be determined as described elsewhere herein.

Examples of such stabilizers are gelatin or albumin, preferably of human origin or obtained from a recombinant source. The stabilizers may be modified by chemical means or by recombinant genetics. In a preferred embodiment of the present invention, it is envisaged to use alcohols, e.g., inositol, mannitol, as cryoprotectant excipients to stabilize proteins during lyophilization.

In a more preferred embodiment of the present invention, the stabilizer may be a non-proteinaceous stabilizing agent comprising hyaluronic acid or polyvinylpyrrolidone or polyethyleneglycol or a mixture of two or more thereof. Such composition is considered to be a safer composition possessing remarkable stability.

In a more preferred embodiment of the present invention, the pharmaceutical composition may comprise the neurotoxic component and a hyaluronic acid or a polyvinylpyrrolidone or a polyetheleneglycol, such composition being optionally pH stabilized by a suitable pH buffer, in particular by a sodium acetate buffer, and/or a cryoprotectant polyalcohol.

Whether or not the pharmaceutical composition comprises, beside the neurotoxin component, additional components such as albumin, hyaluronic acid, a polyvinylpyrrolidone and/or a polyethyleneglycol stabilizer, the pharmaceutical composition retains its potency substantially unchanged for six month, one year, two year, three year and/or four year periods when stored at a temperature between about +8° C. and about −20° C. Additionally, the indicated pharmaceutical compositions may have a potency or percent recovery of between about 20% and about 100% upon reconstitution.

A pharmaceutical composition within the scope of the present invention may include the neurotoxic component one or more additional components. Preferably, the pharmaceutical compositions disclosed herein, has a pH of between about 4 and 7.5 when reconstituted or upon injection, more preferably between about pH 6.8 and pH 7.6 and most preferably between pH 7.4 and pH 7.6. Generally, the pharmaceutical composition of the present invention comprises neurotoxic component in a quantity of about 6 pg to 30 ng, Preferably, the neurotoxic component has a biological activity of 50 to 250 $LD_{50}$ units per ng neurotoxic component, as determined in a mouse $LD_{50}$ assay. More preferably, the neurotoxic component has a biological activity of about 150 $LD_{50}$.

The pharmaceutical composition of the present invention may comprise a neurotoxin, and a hyaluronic acid. The hyaluronic acid stabilizes the neurotoxin. The pharmaceutical compositions disclosed herein may have a pH of between about 4 and 7.5 when reconstituted or upon injection. The hyaluronic acid in the instant pharmaceutical composition is preferably combined with the instant neurotoxic component in a quantity of 0.1 to 10 mg, especially 1 mg hyaluronic acid per ml in a 200 U/ml *botulinum* toxin solution. More preferably, the subject solution also contains a 1-100 mM, especially 10 mM sodium acetate buffer.

In another preferred embodiment, the composition may contain a polyalcohol as cryoprotectant. Examples of polyalcohols that might be used include, e.g., inositol, mannitol and other non-reducing alcohols.

In particular those embodiments of the present invention's pharmaceutical composition not comprising a proteinaceous stabilizer, preferably do not contain trehalose or maltotriose or related sugar or polyhydroxy compounds which are sometimes used as cryoprotectants.

The polyvinylpyrrolidone in the instant pharmaceutical composition is preferably combined with the instant neurotoxic component in a quantity of 10 to 500 mg, especially 100 mg polyvinylpyrrolidone per ml in a 200 U/ml *botulinum* toxin solution. More preferably, the subject solution also contains a 1-100 mM, especially 10 mM sodium acetate buffer.

The polyethyleneglycol in the instant pharmaceutical composition is preferably combined with the instant neurotoxic component in a quantity of 10 to 500 mg, especially 100 mg polyethyleneglycol per ml in a 200 U/ml *botulinum* toxin solution. More preferably, the subject solution also contains a 1-100 mM, especially 10 mM sodium acetate buffer.

Thus, the instant invention encompasses in a more preferred embodiment a neurotoxic component formulated in a pharmaceutical composition, which contains a hyaluronic acid stabilizer or a polyvinylpyrrolidone stabilizer or a polyethyleneglycol stabilizer. Additionally, the pharmaceutical composition may contain a sodium acetate buffer system and/or an alcoholic cryoprotectant.

The following examples are provided by means of illustration only, and are not intended to be limiting.

EXAMPLE 1: *BOTULINUM* TOXIN THERAPY FOR TREATMENT OF CERVICAL DYSTONIA

A 45 year-old male patient suffering from cervical dystonia is evaluated for *botulinum* toxin therapy. After all appropriate examinations an injection scheme is constructed and *botulinum* toxin free of complexing proteins is applied accordingly in a total dose of 300 MU. On re-evaluation after 2 weeks the symptomotology is improved, but there is a need to include additional target muscles and to increase the *botulinum* toxin dose in initially injected target muscles. Two weeks later the patient is re-evaluated again and the treatment result is optimal.

Adverse effects do not occur. So far, on 7 subsequent injection series the treatment results are maintained without any indication of antibody-induced therapy failure.

EXAMPLE 2: *BOTULINUM* TOXIN THERAPY FOR TREATMENT OF BLEPHAROSPASM. SHORT DURATION OF ACTION

A 61 year-old female patient suffering from blepharospasm is treated with a medicament containing the neurotoxic component of the present invention, free of complexing proteins, in a total dose of 48 MU with excellent results. 4 weeks after the injections with the neurotoxic component the effect begins to wane. After 2 more weeks the effect of the treatment has almost completely ceased. Re-Injections are performed 7 weeks after the initial injection series. Therapy with the neurotoxic component is repeated in the initial dose and with identical effects. Therapy with the neurotoxic component is continued for 6 subsequent injection series with excellent therapeutic results and without any indication of antibody-induced therapy failure.

EXAMPLE 3: *BOTULINUM* TOXIN THERAPY FOR TREATMENT OF GENERALISED SPASTICITY. HIGH DOSE APPLICATION

A 35 year-old male patient suffering from hypoxic brain damage with generalized spasticity. The neurotoxic component of the present invention, free of complexing proteins in a total dose of 750 MU, is administered in three aliquots of 250 MU given with 1 day intervals. 2 weeks after the application the condition has improved substantially. Adverse effects, neither local nor regional nor systemic, cannot be detected. On 7 subsequent injection series the therapeutic effect is stable without occurrence of adverse effects. There is no indication of antibody-induced therapy failure.

EXAMPLE 4: COSMETIC USE OF *BOTULINUM* TOXIN. DIFFICULTIES IN CONSTRUCTING THE INJECTION SCHEME AND SHORT DURATION OF ACTION

A 40 year old female client presenting with muscular frowning lines and horizontal frontal lines was treated with 20 MU of *botulinum* toxin free of complexing proteins (i.e. the neurotoxic component of the present invention). 2 weeks later there is an improvement of the symptomotology, but additional injection of 20 MU of *botulinum* toxin are necessary. 2 weeks later the outcome is fully satisfactory for the patient. 4 weeks later the favorable effect starts to wane, so that *botulinum* toxin re-injections in a total dose of 40 MU become necessary. So far, the client has undergone 4 subsequent injection series with total doses of 40 MU each. There is no indication of antibody-induced therapy failure.

The invention claimed is:

1. A method of treating a disease or condition caused by or associated with hyperactive cholinergic innervation of muscles in a patient, the method comprising administering a composition comprising a therapeutically effective amount of a neurotoxic component of a *Clostridium botulinum* toxin complex, the composition being devoid of any other protein component of the *Clostridium botulinum* toxin complex, to remove partially or completely the treated disease or condition symptoms, wherein
   (a) the patient is a human;
   (b) the composition is locally administered by injection of a non-lethal dose to a muscle exhibiting hyperactive cholinergic innervation; and
   (c) the therapeutically effective amount of a non-lethal dose of the neurotoxic component of *Clostridium botulinum* is locally administered to a muscle exhibiting hyperactive cholinergic innervation in a total dosage of from 500 U to 2000 U of the neurotoxic component.

2. The method of claim 1, wherein the composition is locally administered by injection of a non-lethal dose to a muscle exhibiting hyperactive cholinergic innervation at an interval of less than eight weeks, the interval comprising a first treatment and a second treatment, wherein the amount administered in the second treatment can be lower, higher or identical to the amount administered in the first treatment.

3. The method of claim 1, wherein the patient is a human, who has been treated with a *Clostridium botulinum* toxin but who complains about a decrease of the treatment effect and who requires an additional treatment within eight weeks of a previous treatment.

4. A method of treating a disease or condition caused by hyperactive cholinergic innervation of a muscle in a patient, the method comprising administering a composition comprising a therapeutically effective amount of a neurotoxic component of a *Clostridium botulinum* toxin complex, the composition being devoid of any other protein component of the *Clostridium botulinum* toxin complex, to remove partially or completely the treated disease or condition symptoms, wherein
  (a) the patient is a human with a severe movement disorder or severe spasticity;
  (b) the composition is locally administered by injection of a non-lethal dose to a muscle exhibiting hyperactive cholinergic innervation; and
  (c) the therapeutically effective amount of a non-lethal dose of the neurotoxic component of the *Clostridium botulinum* complex administered exceeds a total dosage of 500 U in adults or exceeds 15 U/kg body weight in children.

5. The method of claim 4, wherein the composition is locally administered by injection of a non-lethal dose to a muscle exhibiting hyperactive cholinergic innervation at an interval of less than eight weeks, the interval comprising a first treatment and a second treatment, wherein the amount administered in the second treatment can be lower, higher or identical to the amount administered in the first treatment.

6. The method of claim 1, wherein the disease or condition is or involves dystonia of a muscle.

7. The method of claim 6, wherein the dystonia
  (a) is selected from the group consisting of cranial dystonia, blepharospasm, oromandibular dystonia of the jaw opening or jaw closing type, bruxism, Meige syndrome, lingual dystonia, apraxia of eyelid opening, cervical dystonia, antecollis, retrocollis, laterocollis, torticollis, pharyngeal dystonia, laryngeal dystonia, spasmodic dysphonia of the adductor type, spasmodic dysphonia of the abductor type, spasmodic dyspnea, limb dystonia, arm dystonia, task specific dystonias, writer's cramp, musician's cramps, golfer's cramp, leg dystonia involving thigh adduction, thigh abduction, knee flexion, knee extension, ankle flexion, ankle extension, equinovarus deformity, foot dystonia involving striatal toe, toe flexion, toe extension, axial dystonia, Pisa syndrome, belly dancer dystonia, segmental dystonia, hemidystonia, generalised dystonia, dystonia in Lubag, dystonia in corticobasal degeneration, tardive dystonia, dystonia in spinocerebellar ataxia, dystonia in Parkinson's disease, dystonia in Huntington's disease, dystonia in Hallervorden Spatz disease, dopa-induced dyskinesias/dopa-induced dystonia, tardive dyskinesias/tardive dystonia, paroxysmal dyskinesias/dystonias, kinesiogenic, non-kinesiogenic, and action-induced; or
  (b) involves a clinical pattern selected from the group consisting of torticollis, laterocollis, retrocollis, antecollis, flexed elbow, pronated forearm, flexed wrist, thumb-in-palm and clenched fist.

8. The method of claim 6, wherein the muscle is selected from the group consisting of ipsilateral splenius, contralateral sternocleidomastoid, ipsilateral sternocleidomastoid, splenius capitis, scalene complex, levator scapulae, postvertebralis, ipsilateral trapezius, levator scapulae, bilateral splenius capitis, upper trapezius, deep postvertebralis, bilateral sternocleidomastoid, scalene complex, submental complex, brachioradialis, biceps brachialis, pronator quadratus pronator teres, flexor carpi radialis, flexor carpi ulnaris, flexor pollicis longus, adductor pollicis, flexor pollicis brevis/opponens, flexor digitorum superficialis, and flexor digitorum *profundus*.

9. The method of claim 1, wherein the disease or condition is or involves spasticity of a muscle.

10. The method of claim 9, wherein the spasticity is or is associated with a spastic condition in encephalitis and myelitis relating to autoimmune processes, multiple sclerosis, transverse myelitis, Devic syndrome, viral infections, bacterial infections, parasitic infections, fungal infections, hereditary spastic paraparesis, postapoplectic syndrome resulting from hemispheric infarction, postapoplectic syndrome resulting from brainstem infarction, postapoplectic syndrome resulting from myelon infarction, a central nervous system trauma, a central nervous system hemorrhage, an intracerebral hemorrhage, a subarachnoidal hemorrhage, a subdural hemorrhage, an intraspinal hemorrhage, a neoplasia, post-stroke spasticity, and spasticity caused by cerebral palsy.

11. The method of claim 9, wherein the muscle is a smooth or striated muscle.

12. The method of claim 1, wherein the neurotoxic component is selected from the group consisting of type A, B, C, D, E, F, G and mixtures thereof.

13. A method of treating a disease or condition caused by or associated with hyperactive cholinergic innervation of muscles in a patient, the method comprising administering a composition comprising a therapeutically effective amount of a neurotoxic component of a *Clostridium botulinum* toxin complex to remove partially or completely the treated disease or condition symptoms, wherein
  (a) the patient is a human;
  (b) the composition is locally administered by injection of a non-lethal dose to a muscle exhibiting hyperactive cholinergic innervation; and
  (c) the therapeutically effective amount of a non-lethal dose of the neurotoxic component of *Clostridium botulinum* is locally administered to a muscle exhibiting hyperactive cholinergic innervation in a total dosage of from 500 U to 2000 U of the neurotoxic component.

14. A method of treating a disease or condition caused by hyperactive cholinergic innervation of a muscle in a patient, the method comprising administering a composition comprising a therapeutically effective amount of a neurotoxic component of a *Clostridium botulinum* toxin complex to remove partially or completely the treated disease or condition symptoms, wherein
  a. the patient is a human with a severe movement disorder or severe spasticity;
  b. the composition is locally administered by injection of a non-lethal dose to a muscle exhibiting hyperactive cholinergic innervation; and
  c. the therapeutically effective amount of a non-lethal dose of the neurotoxic component of the *Clostridium botulinum* complex administered exceeds a total dosage of 500 U in adults or exceeds 15 Lag body weight in children.

* * * * *

UNITED STATES PATENT AND TRADEMARK OFFICE
CERTIFICATE OF CORRECTION

PATENT NO. : 10,792,344 B2  
APPLICATION NO. : 15/403670  
DATED : October 6, 2020  
INVENTOR(S) : Matthias Marx et al.

Page 1 of 1

It is certified that error appears in the above-identified patent and that said Letters Patent is hereby corrected as shown below:

In the Claims

Column 22, Line 62: "15 Lag" should read -- U/kg --.

Signed and Sealed this  
Seventeenth Day of November, 2020

Andrei Iancu  
*Director of the United States Patent and Trademark Office*